(12) United States Patent
Matsuo et al.

(10) Patent No.: US 10,478,936 B2
(45) Date of Patent: Nov. 19, 2019

(54) METHOD AND APPARATUS FOR MEASURING SURFACE PROPERTIES OF POLISHING PAD

(71) Applicants: EBARA CORPORATION, Tokyo (JP); Kyushu Institute of Technology, Fukuoka (JP)

(72) Inventors: Hisanori Matsuo, Tokyo (JP); Yoshihiro Mochizuki, Tokyo (JP); Keisuke Suzuki, Fukuoka (JP); Takahiro Tajiri, Fukuoka (JP); Panart Khajornrungruang, Fukuoka (JP)

(73) Assignees: EBARA CORPORATION, Tokyo (JP); Kyushu Institute of Technology, Fukuoka (JP)

( * ) Notice: Subject to any disclaimer, the term of this patent is extended or adjusted under 35 U.S.C. 154(b) by 82 days.

(21) Appl. No.: 14/974,898

(22) Filed: Dec. 18, 2015

(65) Prior Publication Data
US 2016/0184960 A1    Jun. 30, 2016

(30) Foreign Application Priority Data

Dec. 26, 2014  (JP) ................................ 2014-265694

(51) Int. Cl.
*B24B 37/005* (2012.01)
*B24B 49/12* (2006.01)
(Continued)

(52) U.S. Cl.
CPC ............ *B24B 37/005* (2013.01); *B24B 49/12* (2013.01); *G01N 21/55* (2013.01);
(Continued)

(58) Field of Classification Search
CPC ...... B24B 37/005; B24B 49/12; G01N 21/55; G01N 2021/4742; G01N 2201/06113; G01N 2201/0826
(Continued)

(56) References Cited

U.S. PATENT DOCUMENTS 4,353,650 A * 10/1982 Sommargren ....... G01B 11/303
356/369
4,859,062 A * 8/1989 Thurn .................. G01B 11/303
356/446

(Continued)

FOREIGN PATENT DOCUMENTS

JP    09-119822 A    5/1997
JP    10-015807 A    1/1998
(Continued)

OTHER PUBLICATIONS

Tajiri et al.; "Study of polishing pad morphology evaluation by Laser Light Diffraction"; The Japan Society of Mechanical Engineers; Kyushu Student Council Transactions of the 44th Graduate Studies Lecture No. 138-2; © 2013; 5 pages; Partial English Translation.
(Continued)

*Primary Examiner* — Eileen P Morgan
(74) *Attorney, Agent, or Firm* — Baker & Hostetler LLP

(57) ABSTRACT

A polishing pad surface property measuring method which can measure surface properties of a polishing pad that reflect CMP performance by applying a laser beam to the polishing pad at a plurality of incident angles is disclosed. The method includes applying a laser beam to a surface of the polishing pad, and receiving light reflected by the surface of the polishing pad and performing Fourier transform on the
(Continued)

received light to determine surface properties of the polishing pad. The laser beam is applied to the polishing pad at a plurality of incident angles.

13 Claims, 6 Drawing Sheets

(51) Int. Cl.
*G01N 21/55* (2014.01)
*G01N 21/47* (2006.01)

(52) U.S. Cl.
CPC ........... *G01N 2021/4742* (2013.01); *G01N 2201/06113* (2013.01); *G01N 2201/0826* (2013.01)

(58) Field of Classification Search
USPC .......................................... 451/5, 9
See application file for complete search history.

(56) References Cited

U.S. PATENT DOCUMENTS

| | | | | |
|---|---|---|---|---|
| 5,377,002 | A * | 12/1994 | Malin | ............... G01M 11/0278 250/559.45 |
| 5,708,506 | A * | 1/1998 | Birang | ................... B24B 49/12 356/600 |
| 6,670,200 | B2 * | 12/2003 | Ushio | ................... B24B 37/013 257/E21.528 |
| 7,018,269 | B2 | 3/2006 | Anderson | |
| 7,020,306 | B2 * | 3/2006 | Hirose | ................... B24B 37/20 382/108 |
| 7,066,786 | B2 * | 6/2006 | Fujishima | .............. B24B 49/12 451/5 |
| 8,932,883 | B2 | 1/2015 | Matsuo et al. | |
| 9,243,956 | B2 * | 1/2016 | Day | ....................... G01J 3/443 |
| 9,267,842 | B2 * | 2/2016 | Day | ....................... G01J 3/2823 |
| 9,714,864 | B2 * | 7/2017 | Day | ....................... G01J 3/0272 |
| 2001/0015801 | A1 * | 8/2001 | Hirose | .................... B24B 37/20 356/237.2 |
| 2008/0071414 | A1 * | 3/2008 | Fujita | .................... B24B 37/013 700/121 |
| 2010/0159804 | A1 * | 6/2010 | Sampurno | ............ B24B 37/042 451/5 |
| 2014/0364578 | A1 * | 12/2014 | Jang | ..................... C08G 18/758 528/67 |

FOREIGN PATENT DOCUMENTS

| | | |
|---|---|---|
| JP | 2000-505003 A | 4/2000 |
| JP | 2001-223190 A | 8/2001 |
| JP | 2002-116155 A | 4/2002 |
| JP | 2003-338493 A | 11/2003 |
| JP | 2005-244027 A | 9/2005 |
| JP | 2010-052072 A | 3/2010 |
| JP | 2014-172153 A | 9/2014 |
| JP | 2014172154 * | 9/2014 |
| JP | 2014-211440 A | 11/2014 |
| WO | WO 1998/003305 A1 | 1/1998 |

OTHER PUBLICATIONS

Kushida et al.; "Study on evaluation method for surface topography of CMP polishing pad based on optical Fourier transform (4$^{th}$ report) Selection of laser beam incidence angle"; Japan Society for Precision Engineering; 2013; p. 617-618.

* cited by examiner

METHOD AND APPARATUS FOR MEASURING SURFACE PROPERTIES OF POLISHING PAD

CROSS REFERENCE TO RELATED APPLICATION

This document claims priority to Japanese Patent Application Number 2014-265694 filed Dec. 26, 2014, the entire contents of which are hereby incorporated by reference.

BACKGROUND

In recent years, high integration and high density in semiconductor device demands smaller and smaller wiring patterns or interconnections and also more and more interconnection layers. Multilayer interconnections in smaller circuits result in greater steps which reflect surface irregularities on lower interconnection layers. An increase in the number of interconnection layers makes film coating performance (step coverage) poor over stepped configurations of thin films. Therefore, better multilayer interconnections need to have the improved step coverage and proper surface planarization. Further, since the depth of focus of a photolithographic optical system is smaller with miniaturization of a photolithographic process, a surface of the semiconductor device needs to be planarized such that irregular steps on the surface of the semiconductor device will fall within the depth of focus.

Thus, in a manufacturing process of a semiconductor device, it increasingly becomes important to planarize a surface of the semiconductor device. One of the most important planarizing technologies is chemical mechanical polishing (CMP). In the chemical mechanical polishing, using a polishing apparatus, while a polishing liquid containing abrasive particles such as silica ($SiO_2$) or ceria ($CeO_2$) therein is supplied onto a polishing pad, a substrate such as a semiconductor wafer is brought into sliding contact with the polishing pad, so that the substrate is polished.

The polishing apparatus for performing the above CMP process includes a polishing table having a polishing pad, and a substrate holding device, which is referred to as a carrier or a top ring, for holding a substrate such as a semiconductor wafer. By using such a polishing apparatus, the substrate is held and pressed against the polishing pad under a predetermined pressure by the substrate holding device, thereby polishing an insulating film or a metal film on the substrate.

After one or more substrates have been polished, abrasive particles or ground-off particles of the substrate are attached to the surface of the polishing pad, and surface topography or surface condition of the polishing pad is changed, resulting in deterioration in polishing performance. Therefore, as the substrates are repeatedly polished by the same polishing pad, a polishing rate is lowered and nonuniform polishing action is caused. Thus, dressing (conditioning) of the polishing pad is performed by using a dresser to regenerate the surface topography or surface condition of the polishing pad which has deteriorated.

In CMP (Chemical Mechanical Polishing), the surface topography and surface condition of the polishing pad have a large effect on the polishing performance, and thus it has been proposed to measure the surface topography and surface condition of the polishing pad by various measuring methods.

For example, Japanese Laid-open Patent Publication No. 9-119822 discloses a method for measuring the surface roughness of the polishing pad by applying a light beam to a polishing pad.

Further, Japanese Laid-open Patent Publication No. 2014-172153 discloses a method for measuring the surface properties of the polishing pad by applying a laser beam to the polishing pad and obtaining a spatial wavelength spectrum from scattered light reflected and scattered by the polishing pad.

None of prior art documents including Japanese Laid-open Patent Publication No. 9-119822 and Japanese Laid-open Patent Publication No. 2014-172153 addressed to the measurement of the surface roughness, surface properties, etc. of the polishing pad surface, refer to a technology for applying a light beam such as a laser beam to the polishing pad at a plurality of incident angles.

The present inventors have repeated experiments in which a laser beam is applied to a polishing pad to evaluate the surface properties of the polishing pad and have analyzed the results of the experiments. As a consequence, the present inventors have found such a problem that if the surface properties of the polishing pad are not measured using a plurality of incident angles, there are instances in which the surface properties of the polishing pad that truly reflect CMP performance cannot be captured.

SUMMARY OF THE INVENTION

According to an embodiment, there is provided a polishing pad surface property measuring method and apparatus which can measure surface properties of a polishing pad that reflect CMP performance by applying a laser beam to the polishing pad at a plurality of incident angles.

According to another embodiment, there is provided a CMP apparatus for polishing a substrate or dressing a polishing pad under operating conditions that are established based on measured surface properties of the polishing pad.

Embodiments, which will be described below, relate to a polishing pad surface property measuring method and apparatus for measuring surface properties such as surface topography or surface condition of a polishing pad used for polishing a substrate such as a semiconductor wafer.

In an embodiment, there is provided a method of measuring surface properties of a polishing pad, comprising: applying a laser beam to a surface of a polishing pad; and receiving light reflected by the surface of the polishing pad and performing Fourier transform on the received light to determine surface properties of the polishing pad; wherein the laser beam is applied to the polishing pad at a plurality of incident angles.

According to an embodiment, by obtaining the surface properties of the polishing pad at a plurality of incident angles, it is possible to obtain the surface properties of the polishing pad which reflect CMP performance more strongly (with a stronger correlation to CMP performance) than if the surface properties of the polishing pad are obtained at a single incident angle.

Since minute concavities and convexities exist in the surface of the polishing pad, when a laser beam is applied at a high incident angle (an angle nearly parallel to the polishing pad surface), the laser beam reaches the convexities, but is less likely to reach the concavities because of shadows created by the convexities. In this case, when the laser beam is applied at a low incident angle (an angle nearly perpendicular to the polishing pad surface), the laser beam also reaches the concavities, thus making it possible to obtain information about the concavities. In this case, however, the diffracted light from the location very close to the surface of the polishing pad is weakened. Specifically, if a single incident angle is used, information about concavities may be difficult to obtain or the diffracted light from the location very close to the surface of the polishing pad may be weakened, and thus cases where it is difficult to obtain desired pad surface information are expected. On the other hand, by introducing irradiation of the laser beam at many incident angles as proposed by the present invention, it is possible to avoid a lack of information and to obtain desired information.

In an embodiment, the plurality of incident angles of the laser beam are selected from an angular range greater than the Brewster angle for the material of the polishing pad as a measuring object.

According to an embodiment, if the incident angle is smaller than the Brewster angle, there are instances where the reflectance is low and sufficient amount of reflected light is not obtained. Therefore, the incident angle should desirably be greater than the Brewster angle in the present invention.

In an embodiment, the plurality of incident angles of the laser beam are selected depending on the material of the polishing pad as a measuring object, dressing conditions for the surface of the polishing pad, and the type of a dresser member for dressing the polishing pad.

In an embodiment, the plurality of incident angles of the laser beam are adjusted by changing an angle and/or position of a mirror disposed between a light source and the polishing pad.

In an embodiment, the plurality of incident angles of the laser beam are determined by causing the laser beam to be reflected by mirrors provided in different positions between a light source and the polishing pad.

In an embodiment, the plurality of incident angles of the laser beam are adjusted by moving a light source.

In an embodiment, the plurality of incident angles of the laser beam are adjusted by providing a plurality of light sources in different positions.

In an embodiment, the plurality of incident angles of the laser beam are adjusted by a splitter provided between a light source and the polishing pad.

In an embodiment, the plurality of incident angles of the laser beam are adjusted by changing an angle of an optical fiber which emits light with respect to the surface of the polishing pad.

In an embodiment, of the surface properties of the polishing pad that are obtained at the plurality of incident angles of the laser beam, the surface properties that are obtained at some incident angles, rather than all the incident angles, are regarded as representative surface properties of the polishing pad.

In an embodiment, there is provided an apparatus for measuring surface properties of a polishing pad, comprising: an optical system configured to apply a laser beam to a polishing pad at at least two incident angles; and a processing device configured to determine surface properties of the polishing pad by performing Fourier transform on reflected light, from the polishing pad, that is obtained by the optical system.

In an embodiment, the optical system includes a light source, a light emitter, a mirror, and a light receiver, at least one of which is movable.

In an embodiment, the optical system includes a light source, a light emitter, a mirror, and a light receiver, at least one of which comprises the plural ones.

In an embodiment, the optical system includes a light receiver comprising a CCD element or a CMOS element.

In an embodiment, the optical system includes a light emitter comprising an optical fiber.

In an embodiment, there is provided a CMP apparatus comprising: a carrier configured to hold a substrate as an object to be polished and to press the substrate against a polishing pad; a polishing table configured to hold the polishing pad and to rotate the polishing pad; a dresser configured to dress the polishing pad; and the above-described apparatus for measuring surface properties of a polishing pad.

The above-described embodiments offer the following advantages:

(1) By obtaining the surface properties of the polishing pad at a plurality of incident angles, it is possible to obtain the surface properties of the polishing pad which reflect CMP performance more strongly (with a stronger correlation to CMP performance) than if the surface properties of the polishing pad are obtained at a single incident angle.

(2) According to an embodiment, since the surface properties of the polishing pad can be grasped in real time, the following stable operation of CMP can be performed:

1) The cost of consumable materials can be reduced because the polishing pad and the dresser can be used up until the end of their lives.

2) Since an unsteady state of the surface properties of the polishing pad due to some dressing abnormality can promptly be detected and an alarm can be activated, any semiconductor device fabrication failure owing to a CMP performance fault can be minimized.

3) The surface properties of the polishing pad can be maintained in a state required to ensure the CMP performance by changing dressing conditions depending on a change in the surface properties of the polishing pad.

DESCRIPTION OF EMBODIMENTS

Figure 1:
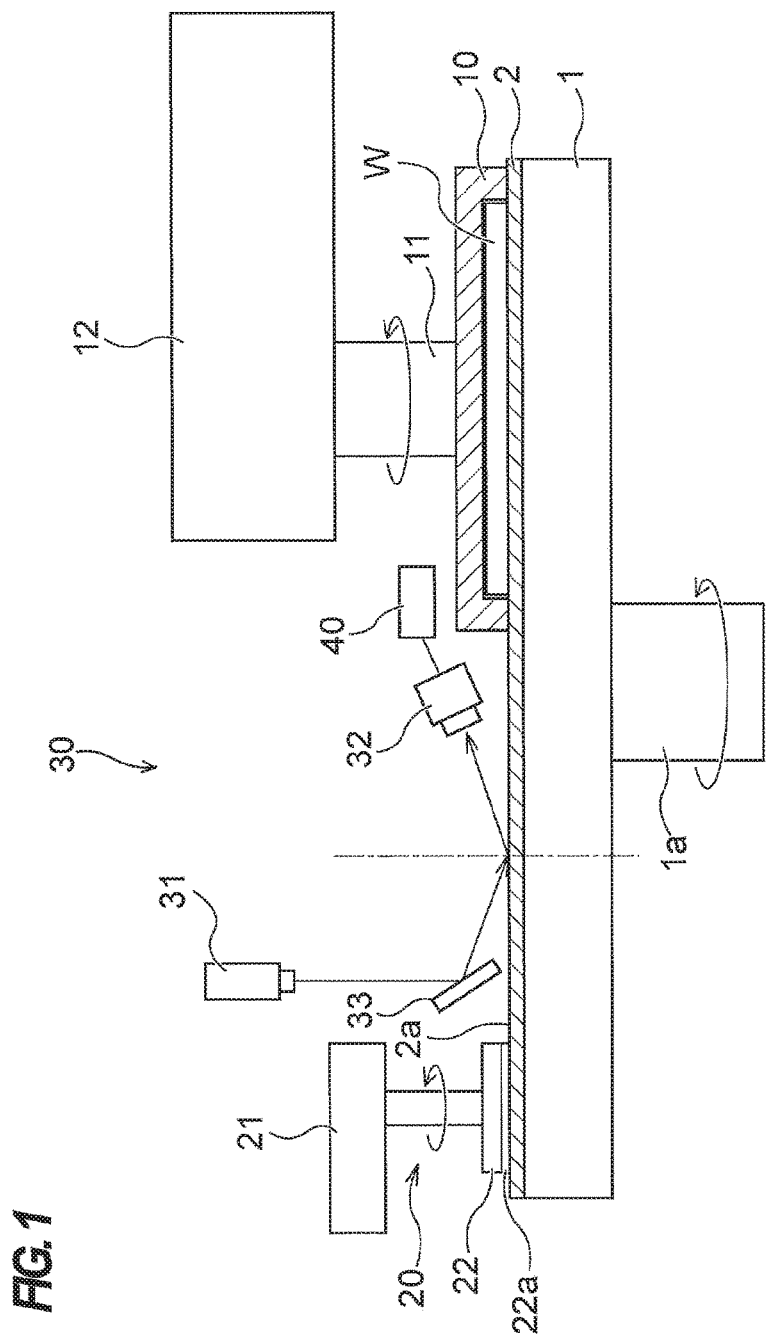
FIG. 1 is a schematic view showing an entire structure of a polishing apparatus for conducting a polishing pad surface property measuring method according to an embodiment.

Embodiments of a method and apparatus for measuring surface properties of a polishing pad will be described below with reference to FIGS. 1 through 11. In FIGS. 1 through 11, identical or corresponding parts are denoted by identical or corresponding reference numerals throughout views, and will not be described in duplication.

FIG. 1 is a schematic view showing an entire structure of a polishing apparatus for conducting a polishing pad surface property measuring method according to an embodiment. As shown in FIG. 1, the polishing apparatus comprises a polishing table 1, and a carrier 10 for holding a substrate W such as a semiconductor wafer as an object to be polished and pressing the substrate W against a polishing pad on the polishing table. The polishing table 1 is coupled via a table shaft 1a to a polishing table rotating motor (not shown) disposed below the polishing table 1. Thus, the polishing table 1 is rotatable about the table shaft 1a. A polishing pad 2 is attached to an upper surface of the polishing table 1. An upper surface of the polishing pad 2 constitutes a polishing surface 2a for polishing the substrate W. The polishing pad 2 comprising SUBA 800, IC-1000, IC-1000/SUBA400 (two-layer cloth) or the like manufactured by the Dow Chemical Company is used. The SUBA 800 is non-woven fabrics bonded by urethane resin. The IC-1000 comprises a pad composed of hard polyurethane foam and having a large number of fine holes (pores) formed in its surface, and is also called a perforated pad. A polishing liquid supply nozzle (not shown) is provided above the polishing table 1 to supply a polishing liquid (slurry) onto the polishing pad 2 on the polishing table 1.

The carrier 10 is connected to a shaft 11, and the shaft 11 is vertically movable with respect to a carrier arm 12. When the shaft 11 moves vertically, the carrier 10 is lifted and lowered as a whole for positioning with respect to the carrier arm 12. The shaft 11 is configured to be rotated by driving a motor (not shown). The carrier 10 is rotated about an axis of the shaft 11.

As shown in FIG. 1, the carrier 10 is configured to hold the substrate W such as a semiconductor wafer on its lower surface. The carrier arm 12 is configured to be pivotable, and thus the carrier 10, which holds the substrate W on its lower surface, is movable from a position at which the carrier 10 receives the substrate to a position above the polishing table 1 by pivotable movement of the carrier arm 12. Then, the carrier 10 holds the substrate W on its lower surface and presses the substrate W against the surface (polishing surface) of the polishing pad 2. At this time, while the polishing table 1 and the carrier 10 are respectively rotated, a polishing liquid (slurry) is supplied onto the polishing pad 2 from the polishing liquid supply nozzle provided above the polishing table 1. The polishing liquid containing silica ($SiO_2$) or ceria ($CeO_2$) as abrasive particles is used. In this manner, while the polishing liquid is supplied onto the polishing pad 2, the substrate W is pressed against the polishing pad 2 and is moved relative to the polishing pad 2 to polish an insulating film, a metal film or the like on the substrate. Examples of the insulating film include $SiO_2$, and examples of the metal film include a Cu film, a W film, a Ta film and a Ti film.

As shown in FIG. 1, the polishing apparatus has a dressing apparatus 20 for dressing the polishing pad 2. The dressing apparatus 20 comprises a dresser arm 21, and a dresser 22 which is rotatably attached to a forward end of the dresser arm 21. The lower part of the dresser 22 comprises a dressing member 22a, and the dressing member 22a has a circular dressing surface. Hard particles are fixed to the dressing surface by electrodeposition or the like. Examples of the hard particles include diamond particles, ceramic particles and the like. A motor (not shown) is provided in the dresser arm 21, and the dresser 22 is rotated by the motor. The dresser arm 21 is coupled to a lifting and lowering mechanism (not shown), and the dresser arm 21 is lowered by the lifting and lowering mechanism to allow the dressing member 22a to be pressed against the polishing surface 2a of the polishing pad 2. Equipments including the polishing table 1, the carrier 10, the dressing apparatus 20 and the like are connected to a controller (not shown), and the rotational speed of the polishing table 1, the rotational speed and the polishing pressure of the carrier 10, the load, the oscillating speed, and the like of the dresser 22 of the dressing apparatus 20 are controlled by the controller.

As shown in FIG. 1, the polishing apparatus has a polishing pad surface property measuring apparatus 30 for measuring surface properties such as surface topography or surface condition of the polishing pad 2. The polishing pad surface property measuring apparatus 30 includes a light source 31 for applying a laser beam to the polishing pad 2, and a light receiver 32 for receiving reflected light that is reflected by the surface of the polishing pad 2. According to the embodiment shown in FIG. 1, the laser beam emitted from the light source 31 is applied via a mirror 33 to the polishing pad 2.

The light receiver 32, which comprises a CCD element or a CMOS element, is disposed above the polishing pad 2. The light receiver 32 is connected to a processing device 40. The processing device 40 has a processing function to convert an intensity distribution (spectrum) of the reflected light received by the light receiver into numerical values correlated to the CMP performance according to a particular processing method. The processing device 40 also has a display function to display the intensity distribution of reflected light and the numerical values correlated to the CMP performance. The processing device 40 may be incorporated in a CMP controller. Signals from the processing device 40 are inputted into the CMP controller.

Figure 2:
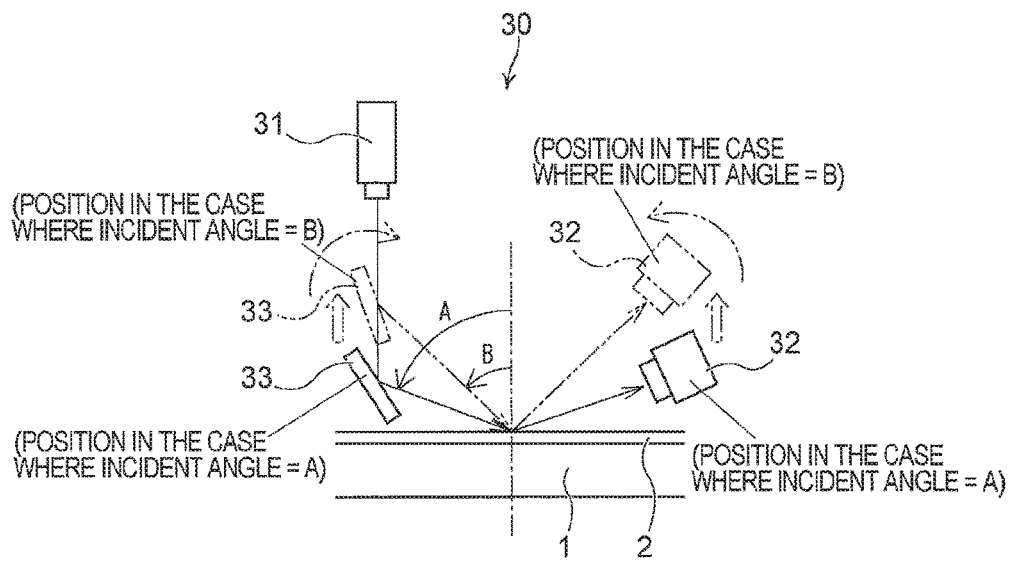
FIG. 2 is a schematic front elevational view showing a first embodiment of the polishing pad surface property measuring apparatus shown in FIG. 1.

FIG. 2 is a schematic front elevational view showing a first embodiment of the polishing pad surface property measuring apparatus 30. In the surface property measuring apparatus 30 shown in FIG. 2, the light source 31 is fixed in position, and the mirror 33 and the light receiver 32 are vertically movable. As shown in FIG. 2, the mirror 33 is movable between a lowered position indicated by the solid lines and an elevated position indicated by the two-dot chain lines. Further, the light receiver 32 is movable between a lowered position indicated by the solid lines and an elevated position indicated by the two-dot chain lines.

In the polishing pad surface property measuring apparatus 30 that is arranged as shown in FIG. 2, when both the mirror 33 and the light receiver 32 are in the lowered position indicated by the solid lines, the laser beam emitted from the light source 31 is reflected by the mirror 33 to change its optical path and is then applied to the polishing pad at an incident angle=A. The light that is reflected by the surface of the polishing pad 2 is received by the light receiver 32.

Further, when both the mirror 33 and the light receiver 32 are in the elevated positions indicated by the two-dot chain lines, the laser beam emitted from the light source 31 is reflected by the mirror 33 to change its optical path and is then applied to the polishing pad at an incident angle=B. The light that is reflected by the surface of the polishing pad 2 is received by the light receiver 32.

In this manner, since the mirror 33 and the light receiver 32 are configured to be movable, the laser beam emitted from the fixed light source (light emitter) 31 can be applied to the polishing pad 2 at a plurality of incident angles.

Figure 3:
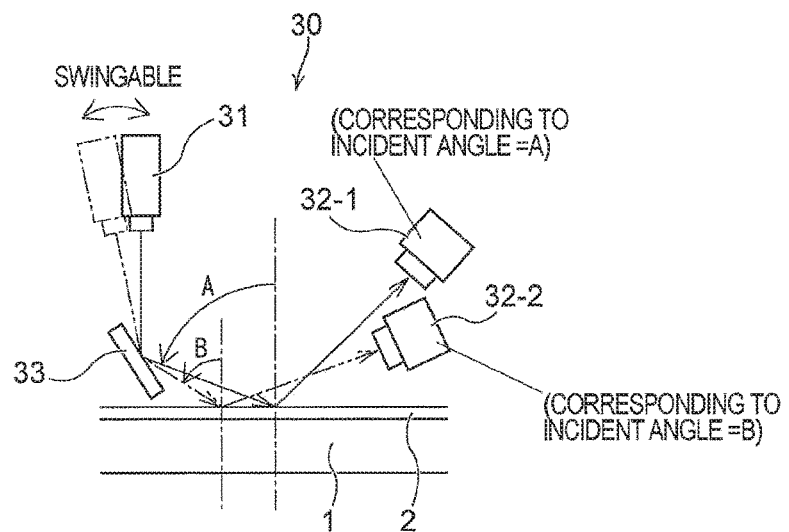
FIG. 3 is a schematic front elevational view showing a second embodiment of the polishing pad surface property measuring apparatus shown in FIG. 1.

FIG. 3 is a schematic front elevational view showing a second embodiment of the polishing pad surface property measuring apparatus 30. In the polishing pad surface property measuring apparatus 30 shown in FIG. 3, the mirror 33 and the light receiver 32 are fixed in position, and the light source 31 is configured to be movable, i.e., swingable. As shown in FIG. 3, the light source 31 is configured to be swingable between a vertical position indicated by the solid lines and a tilted position indicated by the two-dot chain lines. Further, there are provided two light receivers comprising a first light receiver 32-1 disposed in an upper position and a second light receiver 32-2 disposed in a lower position.

In the polishing pad surface property measuring apparatus 30 that is arranged as shown in FIG. 3, when the light source 31 is in the vertical position indicated by the solid lines, the laser beam emitted from the light source 31 is reflected by the mirror 33 to change its optical path and is then applied to the polishing pad 2 at the incident angle=A. The light that is reflected by the surface of the polishing pad 2 is received by the first light receiver 32-1 disposed in the upper position.

Further, when the light source 31 is swung into the tilted position indicated by the two-dot chain lines, the laser beam emitted from the light source 31 is reflected by the mirror 33 to change its optical path and is then applied to the polishing pad 2 at the incident angle=B. The light that is reflected by the surface of the polishing pad 2 is received by the second light receiver 32-2 in the lower position.

In this manner, since the light source (light emitter) 31 is configured to be swung, the angle of the laser beam emitted from the light source (light emitter) 31 can be changed. Thus, the laser beam can be applied via the fixed mirror 33 to the polishing pad 2 at a plurality of incident angles.

Figure 4:
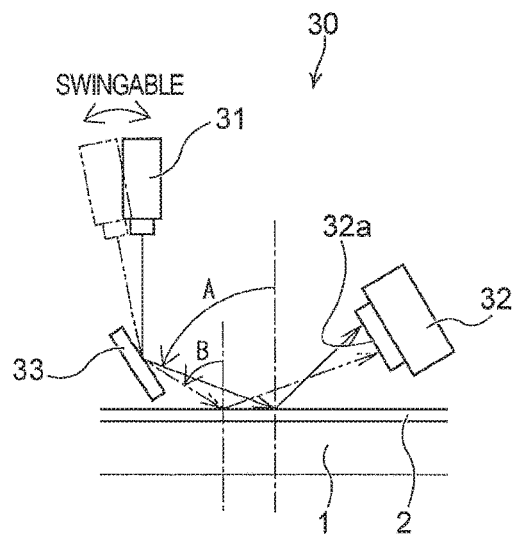
FIG. 4 is a schematic front elevational view showing a third embodiment of the polishing pad surface property measuring apparatus shown in FIG. 1.

FIG. 4 is a schematic front elevational view showing a third embodiment of the polishing pad surface property measuring apparatus 30. In the polishing pad surface property measuring apparatus 30 shown in FIG. 4, the mirror 33 and the light receiver 32 are fixed in position, and the light source 31 is configured to be movable, i.e., swingable. As shown in FIG. 4, the light source 31 is configured to be swingable between the vertical position indicated by the solid lines and the tilted position indicated by the two-dot chain lines. The light receiver 32 has a light receiving surface 32a for receiving the reflected light, and the light receiving surface 32a is set to be greater than the light receiving surfaces of the light receivers shown in FIGS. 2 and 3. Therefore, the light receiver 32 is capable of receiving the reflected light even when reflection angles of the reflected light from the polishing pad 2 differ.

In the polishing pad surface property measuring apparatus 30 that is arranged as shown in FIG. 4, when the light source 31 is in the vertical position indicated by the solid lines, the laser beam emitted from the light source 31 is reflected by the mirror 33 to change its optical path and is then applied to the polishing pad 2 at the incident angle=A. The light that is reflected by the surface of the polishing pad 2 is received by the light receiver 32.

Further, when the light source 31 is swung into the tilted position indicated by the two-dot chain lines, the laser beam emitted from the light source 31 is reflected by the mirror 33 to change its optical path and is then applied to the polishing pad 2 at the incident angle=B. The light that is reflected by the surface of the polishing pad 2 is received by the light receiver 32.

In this manner, since the light source (light emitter) 31 is configured to be swung, the angle of the laser beam emitted from the light source (light emitter) 31 can be changed. Thus, the laser beam can be applied via the fixed mirror 33 to the polishing pad 2 at a plurality of incident angles. The light receiver 32 has a large light receiving surface 32a so that the light receiver 32 can receive all the reflected lights having different reflection angles. The fixed (unmovable) light receiver 32 may be a single light receiver.

Figure 5:
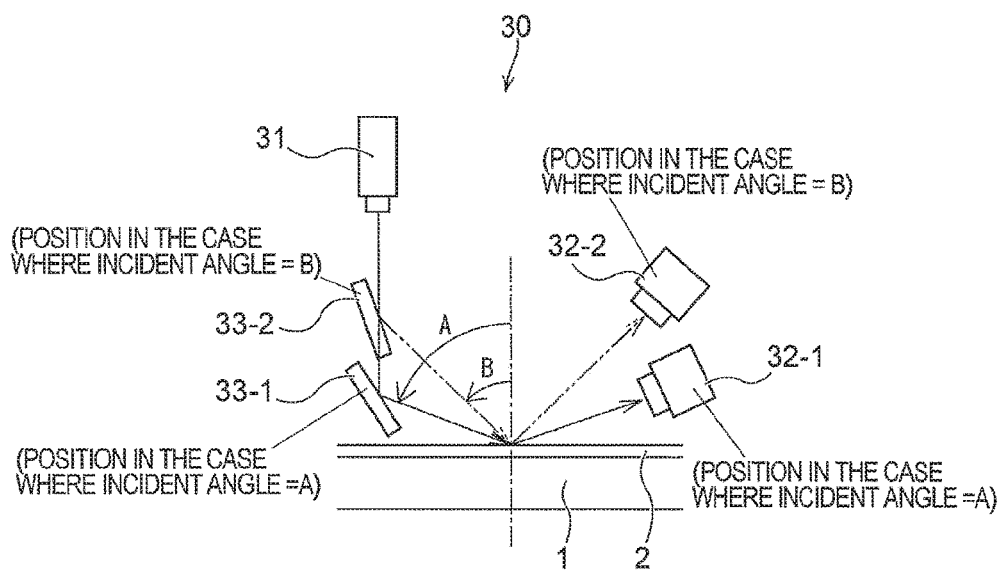
FIG. 5 is a schematic front elevational view showing a fourth embodiment of the polishing pad surface property measuring apparatus shown in FIG. 1.

FIG. 5 is a schematic front elevational view showing a fourth embodiment of the polishing pad surface property measuring apparatus 30. In the surface property measuring apparatus 30 shown in FIG. 5, a plurality of mirrors and a plurality of light receivers are provided. As shown in FIG. 5, there are provided two mirrors comprising a first mirror 33-1 disposed in a lower position and a second mirror 33-2 disposed in an upper position. Further, there are provided two light receivers comprising a first light receiver 32-1 disposed in a lower position and a second light receiver 32-2 disposed in an upper position.

In the polishing pad surface property measuring apparatus 30 that is arranged as shown in FIG. 5, the laser beam emitted from the light source 31 is reflected by the first mirror 33-1 to change its optical path and is then applied to the polishing pad 2 at the incident angle=A. The light that is reflected by the surface of the polishing pad 2 is received by the first light receiver 32-1. Further, the laser beam emitted from the light source 31 is reflected by the second mirror 33-2 to change its optical path and is then applied to the polishing pad 2 at the incident angle=B. The light that is reflected by the surface of the polishing pad 2 is received by the second light receiver 32-2. The mirror 33-2 that reflects the laser beam corresponding to the incident angle B is made of a material permeable to light. In this case, actually, since the laser beam that passes through the mirror 33-2 corresponding to the incident angle B and reaches the mirror 33-1 corresponding to the incident angle A is refracted by the former mirror 33-2, the latter mirror 33-1 should be set to a material, an angle, and a position in consideration of such refraction. In order to simplify drawing, FIG. 5 does not illustrate an optical path that takes refraction into consideration.

Figure 6:
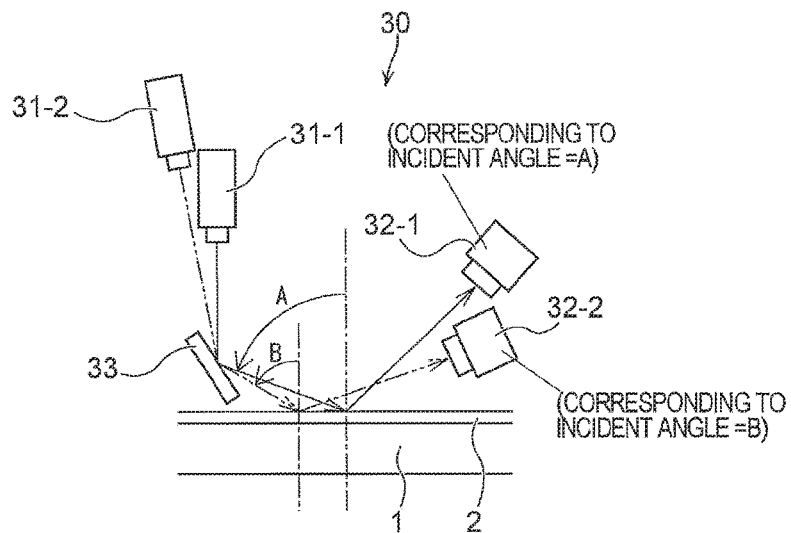
FIG. 6 is a schematic front elevational view showing a fifth embodiment of the polishing pad surface property measuring apparatus shown in FIG. 1.

FIG. 6 is a schematic front elevational view showing a fifth embodiment of the polishing pad surface property measuring apparatus 30. In the polishing pad surface property measuring apparatus 30 shown in FIG. 6, a plurality of light sources and a plurality of light receivers are provided. As shown in FIG. 6, there are provided two light sources comprising a first light source 31-1 disposed in a vertical position and a second light source 31-2 disposed in a tilted position. Further, there are provided two light receivers comprising a first light receiver 32-1 disposed in an upper position and a second light receiver 32-2 disposed in a lower position.

In the polishing pad surface property measuring apparatus 30 that is arranged as shown in FIG. 6, the laser beam emitted from the first light source 31-1 is reflected by the mirror 33 to change its optical path and is then applied to the polishing pad 2 at the incident angle=A. The light that is reflected by the surface of the polishing pad 2 is received by the first light receiver 32-1 disposed in the upper position. Further, the laser beam emitted from the second light source 31-2 disposed in the tilted position is reflected by the mirror 33 to change its optical path and is then applied to the polishing pad 2 at the incident angle=B. The light that is reflected by the surface of the polishing pad 2 is received by the second light receiver 32-2 disposed in the lower position.

In this manner, since the plural light sources 31-1, 31-2 and the plural light receivers 32-1, 32-2 are provided, the laser beam can be applied to the polishing pad 2 at a plurality of incident angles. The light receivers 32-1, 32-2 have respective sizes, positions, and angles selected so as to correspond to the respective incident angles.

Figure 7:
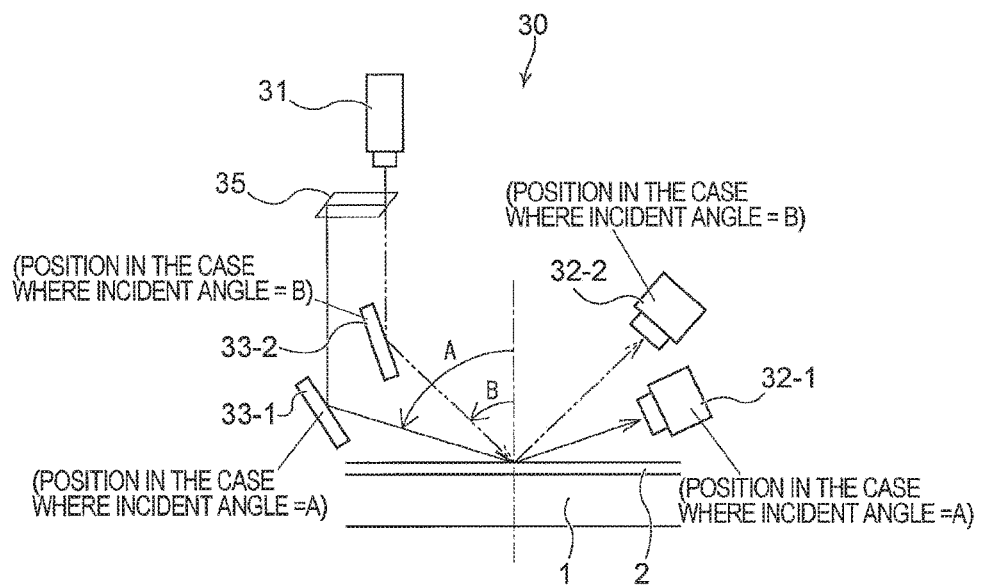
FIG. 7 is a schematic front elevational view showing a sixth embodiment of the polishing pad surface property measuring apparatus shown in FIG. 1.

FIG. 7 is a schematic front elevational view showing a sixth embodiment of the polishing pad surface property measuring apparatus 30. In the polishing pad surface property measuring apparatus 30 shown in FIG. 7, a splitter 35 is provided immediately below the light source 31, and a plurality of mirrors and a plurality of light receivers are provided. As shown in FIG. 7, the splitter 35 is used to divide the laser beam from the single light source 31. There are provided two mirrors comprising a first mirror 33-1 disposed in a lower position and a second mirror 33-2 disposed in an upper position. Further, there are provided two light receivers comprising a first light receiver 32-1 disposed in a lower position and a second light receiver 32-2 disposed in an upper position.

In the polishing pad surface property measuring apparatus 30 that is arranged as shown in FIG. 7, the laser beam emitted from the light source 31 is divided into two laser beams by the splitter 35. One of the laser beams is reflected by the first mirror 33-1 to change its optical path and is then applied to the polishing pad 2 at an incident angle=A. The light that is reflected by the surface of the polishing pad 2 is received by the first light receiver 32-1. The other laser beam is reflected by the second mirror 33-2 to change its optical path and is then applied to the polishing pad 2 at an incident angle=B. The light that is reflected by the surface of the polishing pad 2 is received by the second light receiver 32-2.

In this manner, the splitter 35 is used to divide the laser beam from the single light source 31 into two laser beams, which are reflected at different angles by the two mirrors 33-1, 33-2, so that two incident angles are realized by the single light source.

Figure 8:
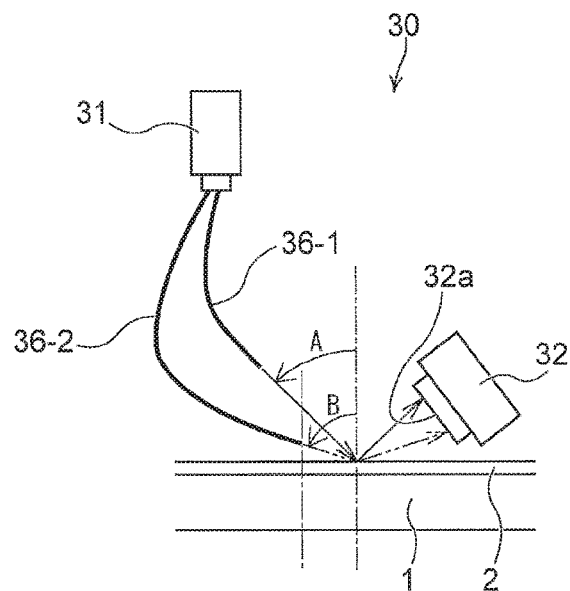
FIG. 8 is a schematic front elevational view showing a seventh embodiment of the polishing pad surface property measuring apparatus shown in FIG. 1.

FIG. 8 is a schematic front elevational view showing a seventh embodiment of the polishing pad surface property measuring apparatus 30. In the polishing pad surface property measuring apparatus 30 shown in FIG. 8, a plurality of optical fibers (light emitters) coupled to the light source 31 are provided. As shown in FIG. 8, two optical fibers 36-1, 36-2 are coupled to the light source 31, and the angles of the two optical fibers 36-1, 36-2 with respect to the polishing pad surface are varied, so that the laser beams can be applied to the polishing pad 2 at a plurality of incident angles.

In the polishing pad surface property measuring apparatus 30 that is arranged as shown in FIG. 8, the laser beam emitted from the light source 31 is guided by the first optical fiber 36-1, and the laser beam emitted from the first optical fiber 36-1 is applied to the polishing pad 2 at an incident angle=A. The light that is reflected by the surface of the polishing pad 2 is received by the light receiver 32. The laser beam emitted from the second optical fiber 36-2 is applied to the polishing pad 2 at an incident angle=B, and the light that is reflected by the surface of the polishing pad 2 is received by the light receiver 32.

In this manner, since the optical fibers (light emitters) 36-1, 36-2 whose shapes are freely alterable are used, the laser beams can be applied to the polishing pad 2 at a plurality of incident angles. The light receiver 32 has a large light receiving surface 32a so that the light receiver 32 can receive all the reflected lights having different reflection angles. Thus, the fixed (unmovable) light receiver 32 may be single. A plurality of light receivers may be provided as with the arrangement shown in FIG. 6.

By using the polishing pad surface property measuring apparatuses 30 that are arranged as shown in FIGS. 2 through 8, the laser beam is applied to the polishing pad at a plurality of incident angles, and a plurality of light beams, which correspond to the respective incident angles, reflected from the pad surface are received by the light receiver or light receivers. The reflected lights that have been received are Fourier-transformed by the processing device 40 to determine a spatial wavelength spectrum of the pad surface, thereby evaluating pad surface properties.

A component of surface roughness is mainly evaluated as one of the pad surface properties. Specifically, after the spatial wavelength spectrum is obtained, a signal intensity in a certain wavelength region (region 1) is integrated, and then a specific wavelength region (region 2) smaller than the region 1 is selected in the range of the region 1 which is considered to contribute to the polishing performance. Then, a signal intensity in the region 2 is integrated, and the ratio of both signal intensities is regarded as an evaluation index. This index is defined as a wavelength constituent ratio to evaluate the pad surface properties.

At this time, it is desirable that the incident angles of the laser beams should be set to be greater than the Brewster angle for the material of the polishing pad (as described later). It is further desirable that suitable incident angles should be selected depending on the type of the pad, the dressing conditions for the pad, and the type of the dressing member (dresser) (as described later). The incident angles are adjusted by making the light source(s), the light emitter (s), the mirror(s) that forms the optical path(s), and the light receiver(s) movable. Depending on the purpose of the application, of the polishing pad surface properties that are obtained corresponding to the plural respective reflection angles, the polishing pad surface properties that are obtained at some incident angles, rather than all the incident angles, may be regarded as representative surface properties of the pad.

As can be understood from the embodiments shown in FIGS. 2 through 8, there is provided a CMP apparatus equipped with an optical system for applying a laser beam to the polishing pad at a plurality of incident angles and a polishing pad surface property measuring apparatus for determining a spatial wavelength spectrum by Fourier-transform of the reflected lights from the polishing pad that are obtained by the optical system. The CMP apparatus can apply a laser beam to the polishing pad at a plurality of incident angles with such an arrangement that at least one of the light source(s), the light emitter(s), the mirror(s), and the light receiver(s) which make up the optical system is movably held or is provided as the plural ones. The light receiver comprises a CCD element or a CMOS element. The light emitter may comprise an optical fiber whose shape is freely alterable so that the incident angle can be easily changed.

The results of experiments for determining the relationship between the incident angles of the laser beam to the polishing pad and the CMP performance will be described below with reference to FIGS. 9 through 11.

Figure 9:
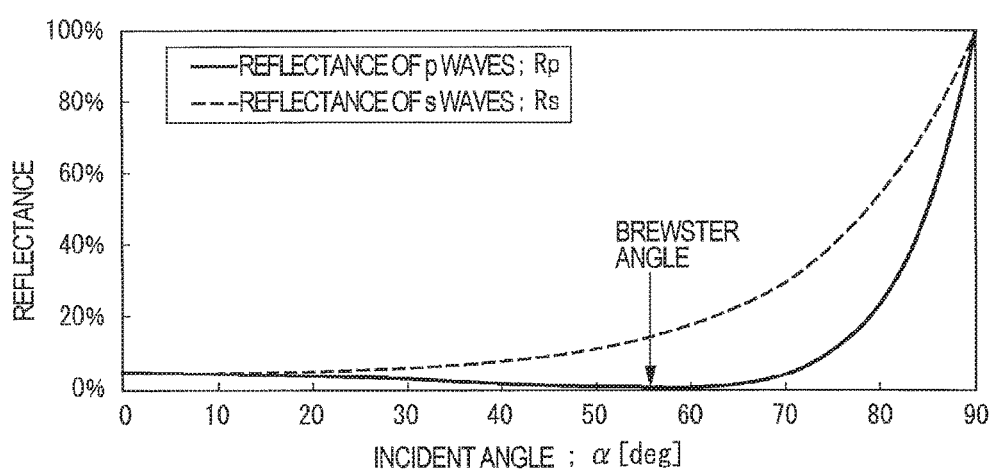
FIG. 9 is a graph showing the relationship between the incident angle of the incident light and the reflectance, which is determined from the refractive indexes of polyurethane as a representative polishing pad material and air.

FIG. 9 is a graph showing the relationship between the incident angle of the incident light and the reflectance, which is determined from the refractive indexes of polyurethane as a representative polishing pad material and air. As seen from FIG. 9, if the incident angle is smaller than the Brewster angle, there are instances where the reflectance is low and sufficient amount of reflected light is not obtained. Therefore, the incident angle should desirably be greater than the Brewster angle. In this case, because the Brewster angle at which the reflectance of p waves (p polarization) becomes zero is about 56.3 degrees, the incident angle that is greater than the Brewster angle is 56.3 degrees or more.

Figure 10:
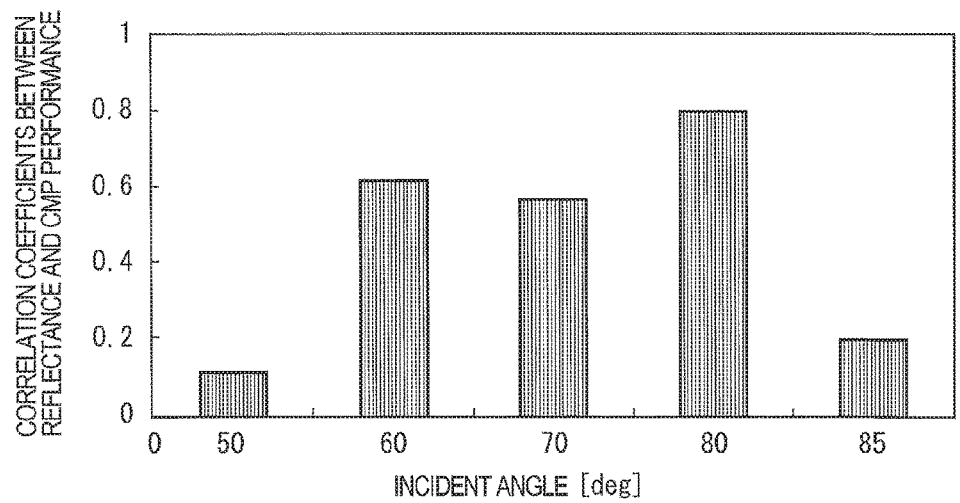
FIG. 10 is a graph showing correlation coefficients between pad surface properties obtained from reflectances and CMP performance for respective incident angles in the case where the incident angle with respect to a general CMP polishing pad is changed.

FIG. 10 is a graph showing correlation coefficients between pad surface properties obtained from reflectances and CMP performance for respective incident angles in the case where the incident angle with respect to a general CMP polishing pad is changed. FIG. 10 indicates that the higher the correlation coefficient is, the stronger the relationship between the obtained pad surface properties and the CMP performance is. As shown in FIG. 10, since the correlation coefficients between the reflectance and the CMP performance are high when the incident angle of the laser beam with respect to the polishing pad is 60 degrees and 80 degrees under certain conditions, it is desirable to select the incident angles of 60 degrees and 80 degrees when a plurality of incident angles are to be set under those conditions.

Figure 11:
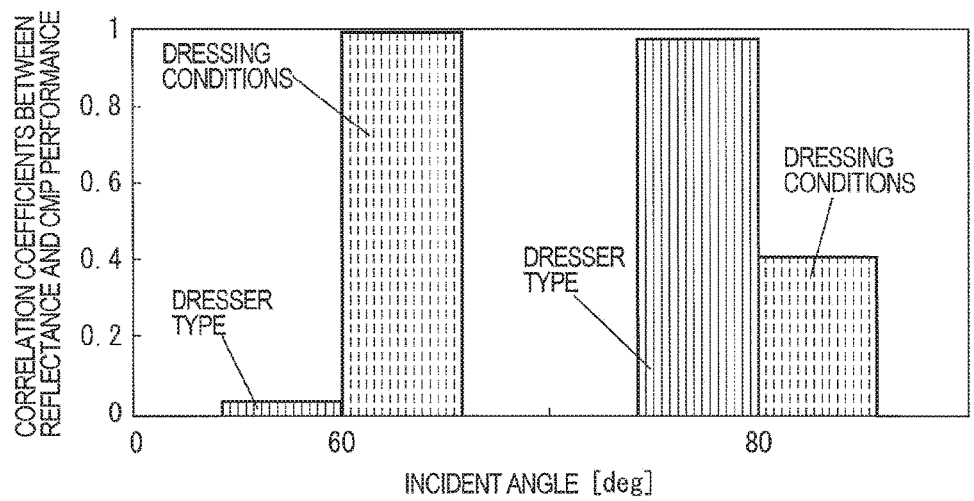
FIG. 11 is a graph showing a comparison result of correlation coefficients between pad surface properties obtained from reflectances and CMP performance in the incident angles of 60 degrees and 80 degrees of the laser beam with respect to the polishing pad in the case where the dressing load at the time of dressing as the dressing conditions is changed and the type of the dresser is changed.

FIG. 11 is a graph showing a comparison result of correlation coefficients between pad surface properties obtained from reflectances and CMP performance in the incident angles of 60 degrees and 80 degrees of the laser beam with respect to the polishing pad in the case where the dressing load at the time of dressing as the dressing conditions is changed and the type of the dresser is changed. It can be seen from FIG. 11 that when the dressing load is changed, the correlation coefficient is high and pad surface properties which reflect the CMP performance more strongly are obtained in the incident angle of 60 degrees, and when the type of the dresser is changed, the correlation coefficient is high and pad surface properties which reflect the CMP performance more strongly are obtained in the incident angle of 80 degrees. Therefore, in this pad, it is desirable to select the incident angles of 60 degrees and 80 degrees if the effects of both the dressing conditions and the dresser type are taken into consideration. In other words, FIG. 11 illustrates the effectiveness of selection of a suitable incident angle of the laser beam depending on the dressing conditions and the type of the dressing member (dresser).

Although certain preferred embodiments of the present invention have been shown and described in detail, it should be understood that various changes and modifications may be made without departing from the scope of the appended claims.

What is claimed is:

1. A method of measuring surface properties of a polishing pad, comprising:
    swinging a light source to apply a laser beam to a surface of a polishing pad at a plurality of incident angles, wherein the plurality of incident angles are different from each other;
    receiving light reflected by the surface of the polishing pad at a plurality of reflection angles; and
    performing a Fourier transform on the received light reflected at the plurality of reflection angles to determine surface properties of the polishing pad.

2. The method of measuring surface properties of a polishing pad according to claim 1, wherein the plurality of incident angles of the laser beam are selected from an angular range greater than the Brewster angle for the material of the polishing pad as a measuring object.

3. The method of measuring surface properties of a polishing pad according to claim 1, wherein the plurality of incident angles of the laser beam are selected depending on the material of the polishing pad as a measuring object, dressing conditions for the surface of the polishing pad, and the type of a dresser member for dressing the polishing pad.

4. An apparatus configured to measure surface properties of a polishing pad, comprising:
    an optical system configured to apply a laser beam to a polishing pad at at least two different incident angles; and
    a processing device configured to determine surface properties of the polishing pad by performing a Fourier transform on light reflected by the polishing pad and received by the optical system;
    wherein the optical system comprises:
        a light source configured to emit the laser beam;
        a first mirror configured to apply the laser beam emitted from the light source to the polishing pad at a first incident angle;
        a second mirror disposed at a second position lower than a first position of the first mirror and configured to apply the laser beam emitted from the light source to the polishing pad at a second incident angle;
        at least two light receivers configured to receive the light reflected by the surface of the polishing pad at a first reflection angle corresponding to the first incident angle and at a second reflection angle corresponding to the second incident angle; and
        wherein the laser beam emitted from the light source passes through the first mirror and is refracted by the first mirror, and the refracted light is applied to the second mirror;
    wherein the Fourier transform is performed on the received light reflected at the first and second reflection angles to determine the surface properties of the polishing pad by the processing device.

5. The apparatus configured to measure surface properties of a polishing pad according to claim 4, wherein the at least one light receiver comprises a CCD element or a CMOS element.

6. A CMP apparatus comprising:
    a carrier configured to hold a substrate as an object to be polished and to press the substrate against a polishing pad;
    a polishing table configured to hold the polishing pad and to rotate the polishing pad;
    a dresser configured to dress the polishing pad; and
    the apparatus configured to measure surface properties of a polishing pad according to claim 4.

7. The apparatus configured to measure surface properties of a polishing pad according to claim 4, wherein the optical system further comprises a splitter provided between the first mirror and the light source, the splitter being configured to divide the laser beam emitted from the light source.

8. A method of measuring surface properties of a polishing pad, comprising:
    moving a mirror configured to reflect a laser beam emitted from a light source and apply the reflected laser beam to a surface of a polishing pad at a plurality of incident angles, wherein the plurality of incident angles are different from each other;

receiving light reflected by the surface of the polishing pad at a plurality of reflection angles; and performing a Fourier transform is performed on the received light reflected at the plurality of reflection angles to determine surface properties of the polishing pad.

9. The method of measuring surface properties of a polishing pad according to claim 8, wherein the plurality of incident angles of the laser beam are selected from an angular range greater than the Brewster angle for the material of the polishing pad as a measuring object.

10. The method of measuring surface properties of a polishing pad according to claim 8, wherein the plurality of incident angles of the laser beam are selected depending on the material of the polishing pad as a measuring object, dressing conditions for the surface of the polishing pad, and the type of a dresser member configured to dress the polishing pad.

11. An apparatus configured to measure surface properties of a polishing pad, comprising:

an optical system configured to apply at least two laser beams to a polishing pad at at least two different incident angles; and a processing device configured to determine surface properties of the polishing pad by performing a Fourier transform on light reflected by the polishing pad and received by the optical system;

wherein the optical system comprises:
 a first light source configured to emit a first laser beam;
 a second light source provided at a second position different from a first position of the first light source and configured to emit a second laser beam;
 a mirror configured to reflect the first laser beam emitted from the first light source and to apply the first laser beam to the polishing pad at a first incident angle, and configured to reflect the second laser beam emitted from the second light source and to apply the second laser beam to the polishing pad at a second incident angle; and
 at least two light receivers configured to receive the light reflected by the surface of the polishing pad at a first reflection angle corresponding to the first incident angle and at a second reflection angle corresponding to the second incident angle;

wherein the Fourier transform is performed on the received light reflected at the first and second reflection angles to determine the surface properties of the polishing pad by the processing device.

12. The apparatus configured to measure surface properties of a polishing pad according to claim 11, wherein the at least one light receiver comprises a CCD element or a CMOS element.

13. An apparatus configured to measure surface properties of a polishing pad, comprising:

an optical system configured to apply a laser beam to a polishing pad at at least two different incident angles; and a processing device configured to determine surface properties of the polishing pad by performing a Fourier transform on light reflected by the polishing pad and received by the optical system;

wherein the optical system comprises:
 a light source configured to emit the laser beam;
 a first optical fiber coupled to the light source and configured to apply the laser beam emitted from the light source to the polishing pad at a first incident angle; and
 a second optical fiber coupled to the light source and configured to apply the laser beam emitted from the light source to the polishing pad at a second incident angle; and
 at least two light receivers configured to receive the light reflected by the surface of the polishing pad at a first reflection angle corresponding to the first incident angle and at a second reflection angle corresponding to the second incident angle;

wherein the Fourier transform is performed on the received light reflected at the first and second reflection angles to determine the surface properties of the polishing pad by the processing device.

* * * * *